United States Patent [19]

Puppe et al.

[11] 4,359,565

[45] Nov. 16, 1982

[54] VINYLSILICONE PASTES FOR DENTAL IMPRESSION

[75] Inventors: Lothar Puppe; Reiner Voigt, both of Leverkusen; Manfred Borgardt, Wuppertal; Hans-Heinrich Moretto, Cologne; Bernard Munchenbach, Leverkusen, all of Fed. Rep. of Germany

[73] Assignee: Bayer Aktiengesellschaft, Leverkusen, Fed. Rep. of Germany

[21] Appl. No.: 288,076

[22] Filed: Jul. 29, 1981

[30] Foreign Application Priority Data

Aug. 23, 1980 [DE] Fed. Rep. of Germany ....... 3031894

[51] Int. Cl.$^3$ ............................................ C08G 77/06
[52] U.S. Cl. ...................................... 528/15; 528/31; 528/14; 528/16; 528/18; 528/32; 524/423; 524/493; 524/588
[58] Field of Search ................. 528/15, 31, 32, 14, 528/16, 18, 23; 260/37 SB; 524/423, 493, 588

[56] References Cited

U.S. PATENT DOCUMENTS 3,950,300 4/1976 Hirtmair et al. ...................... 528/15
4,035,453 7/1977 Hirtmair et al. ...................... 528/15
4,273,902 6/1981 Tomioka et al. ...................... 528/31

FOREIGN PATENT DOCUMENTS 2926405 1/1980 Fed. Rep. of Germany .
2262955 10/1975 France .
2400052 3/1979 France .

OTHER PUBLICATIONS

Ullmanns Encyklopadie Der Technischen Chemie, 4, Aufalge, Band 13, Verlag Chemie, 1977, 533–534.

Primary Examiner—Melvyn I. Marquis
Attorney, Agent, or Firm—Sprung, Horn, Kramer & Woods

[57] ABSTRACT

In a polysiloxane-based dental composition which crosslinks by an addition reaction and hardens at room temperature, the composition comprising
(a) an organopolysiloxane with at least two vinyl groups in the molecule,
(b) an organohydridopolysiloxane,
(c) a catalyst to accelerate the addition reaction, and
(d) a hydrophobic filler, the improvement which comprises including therein
(e) an aluminosilicate containing finely divided palladium. This removes any by-product hydrogen and results in a smoother surface on any plaster of Paris moldings made from the hardened composition.

5 Claims, No Drawings

VINYLSILICONE PASTES FOR DENTAL IMPRESSION

The present invention relates to vinylsilicone pastes which crosslink by an addition reaction and are used for producing accurate impressions of teeth. These pastes are two-component silicone rubber systems which vulcanize in the cold and in which a base paste containing the crosslinking agent is mixed with a catalyst paste and crosslinks after 2–5 minutes at room temperature.

Silicone pastes for dental impressions are widely known. In general, they consist of a silicone oil which is based on a polydimethylsiloxane with hydroxyl end groups and is mixed with fillers, and which, because there are many methods of application, is available in various consistencies, and a liquid or pasty hardener component which contains a metal salt of a monocarboxylic acid as the catalyst and a silicic acid ester as the crosslinking agent.

These two components are also mixed with one another before use and crosslink at room temperature in the course of 2–5 minutes as the result of a polycondensation reaction. In addition to the crosslinked silicone rubber, small amounts of alcohol are also formed and diffuse slowly out of the rubber and cause linear shrinkage, which leads to inaccurate impressions.

The linear shrinkage of vinylsilicone impression compositions, the preparation of which has only been known for a few years, is considerably less. These compositions consist of two pastes, that is to say a base paste containing silicone oil, filler and crosslinking agent, and a catalyst paste containing silicone oil, filler and catalyst.

In this case, the silicone oil is a polydimethylsiloxane with vinyl end groups. The crosslinking agent contains the reactive SiH groups and the catalyst consists of a platinum complex. In addition to the relatively high dimensional accuracy of the model, with this system it is easier to meter in the base paste and catalyst paste as a result of the pastes having the same viscosity and the two pastes being formulated to give a mixing ratio of 1:1, and the pastes are completely flavorless and odorless.

The disadvantage of the vinylsilicone impression compositions is the evolution of hydrogen gas when a plaster of Paris paste is cast in the crosslinked impression, and the defective surface of the plaster of Paris model thereby caused. This hydrogen gas is formed after the reaction of the vinyl groups in the silicone oil with the SiH groups of the crosslinking agent, from the SiH groups which have not been used since they are present in excess, and its formation is promoted by the moisture of the plaster of Paris paste and by the platinum catalyst.

The damaged surface of the plaster of Paris model has a large number of small craters, and so the model must be regarded as useless. A significant improvement in the situation is achieved if the impression is left to stand for at least two hours after it has been taken or is degassed by heating under reduced pressure, before casting the plaster of Paris paste. However, these operations are very time-consuming or require particular care if the dimensional accuracy of the model is not to be impaired.

German Offenlegungsschrift No. 29 26 405 describes a process which attempts to avoid these disadvantages. In this process, palladium or a palladium alloy is added to the crosslinking paste and/or catalyst paste in order thus to utilize the known absorption of hydrogen onto palladium.

In contrast, according to the invention, the use of palladium-containing zeolite in the crosslinking paste and/or catalyst paste provides advantages. The palladium is in a particularly finely divided form, which has an extremely advantageous effect on the absorption of excess hydrogen gas without adversely influencing the crosslinking reaction and the storage stability of the composition. The use of toxicologically unacceptable metal dusts is avoided. In addition, zeolite absorbs traces of moisture in the fillers, so that additional evolution of hydrogen gas from this source is reliably prevented.

According to the invention, this deficiency is thus remedied without problems by using palladium-containing zeolite in the crosslinking paste and/or catalyst paste. The palladium is particularly finely divided in this zeolite, which furthermore can also absorb traces of moisture from the fillers, and this fine division has an extremely advantageous effect on the absorption of excess hydrogen gas without adversely influencing the crosslinking reaction and the storage stability of the composition.

The present invention thus relates to dental compositions which are based on polysiloxane, and can be hardened at room temperature, and which crosslink by an addition reaction and contain (a) organopolysiloxanes with two or more vinyl groups in the molecule, (b) organohydridopolysiloxanes, (c) a catalyst to accelerate the addition reaction and (d) hydrophobic fillers and, if appropriate, other customary additives, characterized in that (e) aluminosilicates which contain finely divided palladium and/or very finely divided palladium alloys are also added to the compositions.

The vinylsilicone pastes according to the invention are thus distinguished for the production of accurate impressions of teeth by their faithful reproduction of detail on the plaster of Paris model, after the crosslinking paste and catalyst paste have been mixed thoroughly and introduced into the cavity of the mouth and have solidified therein and a plaster of Paris paste has been cast in the impression and hardened to give a model.

The starting substances of the vinylsilicone pastes according to the invention are silicone oil (a), fillers (b), crosslinking agents (c), catalyst (d), colorants (e) and, finally, palladium-containing zeolite (f).

The silicone oil (a) is a polydimethylsiloxane which has vinyl end groups and a viscosity which can be in the range from 1,000 to 100,000 mPas at 25° C., depending on the desired consistency of the formulated pastes.

By the fillers (b) there are understood quartz flour and cristobalite flour, calcium sulphate, diatomaceous earth and precipitated and pyrogenically produced silicon dioxide.

The crosslinking agent (e) is a polydimethylsiloxane which has, in its molecule, hydrogen atoms on at least two silicon atoms.

The siloxane copolymers which have different degrees of polymerization and are terminated by trialkylsilyl or dialkylhydridosilyl groups are known.

The catalyst (d) is a platinum complex which has been prepared from hexachloroplatinic-IV acid. These compounds are also known per se.

Colorants (e) are used to differentiate between the base paste and catalyst paste and as a mixing control. Inorganic and organic coloured pigments are preferred.

The zeolites employed for the compositions according to the invention are naturally occurring or synthetic crystalline aluminosilicates with the following general oxide formula:

in which
M′=Li, Na, K etc. and
M″=Mg, Ca, Sr etc.
and are described, for example, in D. W. Breck, Zeolite Molecular Sieves, John Wiley & Sons, Inc. New York 1974.

They are characterized by a rigid, three-dimensional frame work consisting of $SiO_4$ and $AlO_4$ tetrahedra. Inside this frame work are large adsorption cavities which are connected to one another by channels, the so-called pores. Polar or polarizable molecules with diameters less than the pore diameter of the zeolite in question can be reversibly adsorbed in the adsorption cavities. Water is preferentially adsorbed, which is why zeolites are highly effective drying agents.

The $AlO_4$ tetrahedra present in the matrix each give rise to a negative charge, which is balanced by cations. The cations present in the zeolite can be exchanged, it is being possible to influence, by ion exchange, the pore diameters, the adsorption properties and the catalytic behavior according to the nature of the metal cations exchanged.

Some representatives of the transition metals which are present as cations in the zeolite after ion exchange can be reduced to the metals with reducing agents. Highly disperse metals are thereby obtained in the crystalline aluminosilicate matrix.

The vinylsilicone pastes according to the invention contain anhydrous zeolites which have a faujasite structure and carrying finely divided metallic palladium. Synthetic faujasite has the general composition:

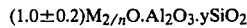

Synthetic faujasites with values of y of 2 to 3 are generally called zeolite X, and those with values of y of 3 to 6 are called zeolite Y.

The preparation of palladium-containing zeolites has already been described elsewhere, for example H. S. Sherry, The Ion Exchange, Volume 2 pages 89–133, New York, 1969, and is not a subject of the present invention.

The zeolites employed in general contain about 0.01% by weight to 5% by weight of present per se or as palladium alloy, preferably 0.1 to 2% by weight. A total of about 0.1% by weight of zeolites to 5% by weight of zeolites, preferably about 0.3% by weight of zeolites to 2% by weight of zeolites, is added to the paste, so that the total composition contains about 0.5 to 100 ppm, preferably 5 to 50 ppm, of palladium.

The following examples, in which all the parts denote parts by weight, illustrate the invention.

EXAMPLE 1

The base paste was prepared by mixing 450 parts of polydimethylsiloxane which has vinyl end groups and a viscosity of 10,000 mPas at 25° C., 50 parts of polydimethylsiloxane which has dimethylhydridosilyl end groups and a viscosity of 50 mPas at 25° C., 350 parts of very fine quartz flour, 125 parts of calcium sulphate, 20 parts of pyrogenically produced silicic acid with a specific surface area, measured by the BET method, of 50 m²/g and 5 parts of organic colored pigment in a kneader.

The catalyst paste was prepared by mixing 500 parts of polydimethylsiloxane which has vinyl end groups and a viscosity of 10,000 mPas at 25° C., 350 parts of very fine quartz flour, 125 parts of calcium sulphate, 24.8 parts of pyrogenically produced silicic acid with a specific surface area, measured by the BET method, of 50 m²/g and 0.2 part of a platinum-siloxane complex in a kneader.

15 g of base paste and 15 g of catalyst paste were mixed thoroughly for 30 seconds on a mixing slab and the mixture was introduced into the mouth on an impression spoon and under a suitable pressure. The mixture hardens to an elastomer within 5 minutes. After removal from the mouth and washing, a plaster of Paris suspension, prepared by mixing 100 parts of calcium sulphate hemihydrate with 30 parts of water, was cast in the impression. 30 minutes later, the plaster of Paris model formed was taken out of the impression. The model was strewn with small craters and was therefore useless.

EXAMPLE 2

The base paste was prepared in a kneader by mixing 450 parts of polydimethylsiloxane which has vinyl end groups and a viscosity of 10,000 mPas at 25° C., 50 parts of polydimethylsiloxane with dimethylhydridosilyl end groups and a viscosity of 50 mPas at 25° C., 350 parts of very fine quartz flour, 120 parts of calcium sulphate, 20 parts of pyrogenically produced silicic acid with a specific surface area, measured by the BET method, of 50 m²/g, 5 parts of organic colored pigment and 5 parts of zeolite with a palladium content of 0.2%.

This base paste was mixed with the catalyst paste from Example 1 in a weight ratio of 1:1, and an impression and then a plaster of Paris model were produced as in Example 1.

The surface of this plaster of Paris model was not damaged at all.

EXAMPLE 3

The catalyst paste was prepared in a kneader by mixing 500 parts of polydimethylsiloxane which has vinyl end groups and a viscosity of 10,000 mPas at 25° C., 350 parts of very fine quartz flour, 125 parts of calcium sulphate, 23.8 parts of pyrogenically produced silicic acid with a specific surface area, measured by the BET method, of 50 m²/g, 0.2 part of a platinum-siloxane complex and 1 part of zeolite with a palladium content of 1%.

This catalyst paste was mixed with the base paste from Example 1 in a weight ratio of 1:1, and an impression and then a plaster of Paris model were produced as in Example 1.

The surface of this plaster of Paris model was also perfectly smooth.

EXAMPLE 4

The base paste was prepared in a kneader by mixing 380 parts of polydimethylsiloxane which has vinyl end groups and a viscosity of 10,000 mPas at 25° C., 70 parts of polydimethylsiloxane which has vinyl end groups and a viscosity of 1,000 mPas at 25° C., 50 parts of polydimethylhydridosiloxane which has dimethylhydridosilyl end groups and a viscosity of 50 mPas at 25° C., 300 parts of very fine quartz flour, 190 parts of diatomaceous earth, 5 parts of organic colored pigments and 5 parts of zeolite containing 0.05% of palladium.

The catalyst paste was prepared by mixing in a kneader and contained 400 parts of polydimethylsiloxane with vinyl end groups and a viscosity of 10,000 mPas at 25° C., 100 parts of polydimethylsiloxane with vinyl end groups and a viscosity of 1,000 mPas at 25° C., 300 parts of very fine quartz flour, 190 parts of diatomaceous earth, 0.2 part of a platinum-siloxane complex and 5 parts of zeolite containing 0.05% of palladium. The two pastes were mixed in a weight ratio of 1:1 and an impression and a plaster of Paris model were produced as in Example 1. The plaster of Paris model had an even, smooth surface.

It will be appreciated that the instant specification and examples are set forth by way of illustration and not limitation, and that various modifications and changes may be made without departing from the spirit and scope of the present invention.

We claim:

1. In a polysiloxane-based dental composition which crosslinks by an addition reaction and hardens at room temperature, the composition comprising
    (a) an organopolysiloxane with at least two vinyl groups in the molecule,
    (b) an organohydridopolysiloxane,
    (c) a catalyst to accelerate the addition reaction, and
    (d) a hydrophobic filler, the improvement which comprises including therein
    (e) an aluminosilicate containing finely divided palladium.

2. A composition according to claim 1, wherein the palladium is present as an alloy.

3. A composition according to claim 1, wherein the aluminosilicate is zeolite of the faujasite type.

4. A composition according to claim 1, containing about 0.5 to 100 ppm of palladium.

5. A composition according to claim 3, wherein the aluminosilicate is present in about 0.1 to 5% by weight of the composition and it contains about 0.01 to 5% by weight of palladium.

* * * * *